Figure 1:
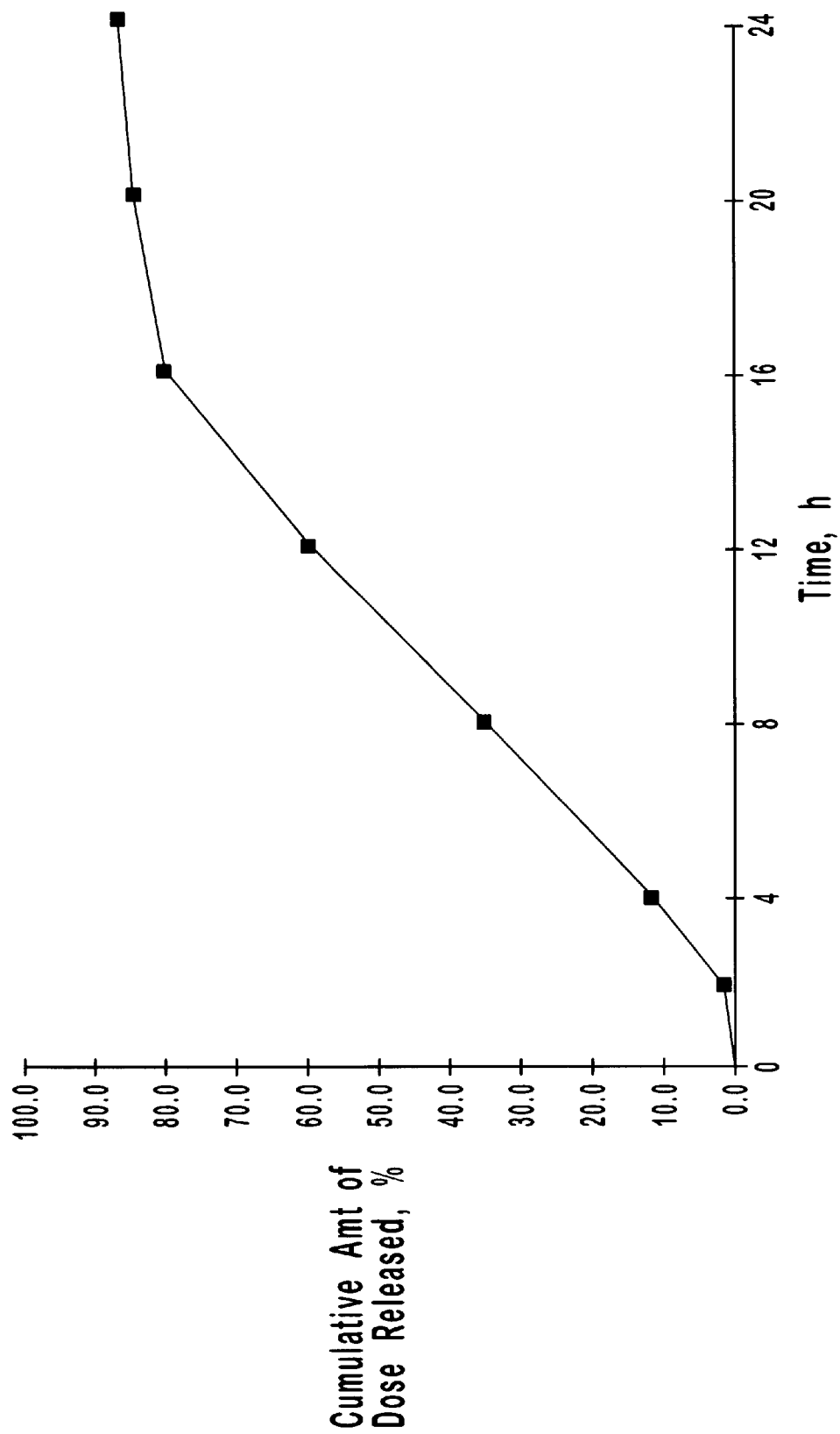

United States Patent [19]

Guittard et al.

[11] Patent Number: 6,124,355

[45] Date of Patent: *Sep. 26, 2000

[54] OXYBUTYNIN THERAPY

[76] Inventors: George V. Guittard; Francisco Jao; Susan M. Marks; David J. Kidney; Fernando E. Gumucio, all of P.O. Box 10950, Palo Alto, Calif. 94303-0802

[*] Notice: This patent is subject to a terminal disclaimer.

[21] Appl. No.: 09/078,192

[22] Filed: May 13, 1998

Related U.S. Application Data

[63] Continuation-in-part of application No. 08/806,773, Feb. 26, 1997, which is a continuation-in-part of application No. 08/706,576, Sep. 5, 1996, which is a continuation-in-part of application No. 08/445,849, May 22, 1995, Pat. No. 5,674,895.

[51] Int. Cl.$^7$ ................................................. A01N 37/44
[52] U.S. Cl. .......................... 514/534; 424/468; 424/474; 424/475; 424/479; 424/480; 424/484; 424/486
[58] Field of Search ........................ 514/534, 579, 514/646, 663, 727, 729, 730; 424/468, 474, 475, 479, 480, 484, 486

[56] References Cited

U.S. PATENT DOCUMENTS

| | | | |
|---|---|---|---|
| 2,799,241 | 7/1957 | Wurster et al. | 118/24 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,111,202 | 9/1978 | Theeuwes et al. | 128/260 |
| 4,200,098 | 4/1980 | Ayer et al. | 128/260 |
| 4,285,987 | 8/1981 | Ayer et al. | 427/3 |
| 4,327,725 | 5/1982 | Cortese et al. | 128/260 |
| 4,612,008 | 9/1986 | Wong et al. | 604/892 |
| 4,783,337 | 11/1988 | Wong et al. | 424/468 |
| 4,816,263 | 3/1989 | Ayer et al. | 424/468 |
| 4,824,675 | 4/1989 | Wong et al. | 424/438 |
| 4,863,456 | 9/1989 | Stephens et al. | 604/892.1 |
| 4,902,514 | 2/1990 | Barclay et al. | 424/473 |
| 5,399,359 | 3/1995 | Baichwal | 424/464 |
| 5,674,895 | 10/1997 | Guittard et al. | 514/534 |
| 5,840,754 | 11/1998 | Guittard et al. | 514/534 |
| 5,912,268 | 6/1999 | Guittard et al. | 514/534 |

OTHER PUBLICATIONS

Grafton, P., "General Principles for Designing with Plastics" Modern Plastics Encyclopedia, vol. 46, pp. 62–71 (1969–70).
Remington's Pharmaceutical Sciences, 14th Ed., pp. 1626–1680 (1970).
Wurster, Dale E., "Air–Suspension Technique of Coating Drug Particles" J. Am. Phar. Assoc. Sci. Ed., vol. 48, pp. 451–454 (Aug. 1959).
Wurster, Dale E., "Preparation of Compressed Tablet Granulations by the Air–Suspension Technique II" J. Am. Phar. Assoc., vol. 49, No. 2, pp. 82–84 (Feb. 1960).
Chemical Abstracts, vol. 120; No. 18, May 2, 1994, Abstract No. 227011.
Chemical Abstracts, vol. 120; No. 14, Apr. 4, 1994, Abstracts No. 173499.
International Journal of Pharmaceutics; 62 (1990); pp. 143–151.
USP XXI/NF XVII (1990), The United States Pharmacopeia/The National Formulary; pp. 1578–1579.
USP 23—Test Solutions; pp. 2052–2053.
Remington's Pharmaceutical Sciences (1985); 17th Ed., Chapter 35; pp. 653–666.
USP 23/NF 18 (1995); The United States Pharmacopeia/The National Formulary; pp. 1791–1796.
Handbook of Common Polymers, by Scott/Roff (1971); pp. 79–81.

Primary Examiner—Michael A. Williamson
Attorney, Agent, or Firm—Paul L. Sabatine; Steven F. Stone

[57] ABSTRACT

A composition comprising oxybutynin, a dosage form comprising oxybutynin, and a method for administering oxybutynin are disclosed for oxybutynin therapy.

21 Claims, 2 Drawing Sheets

OXYBUTYNIN THERAPY

CROSS REFERENCE TO RELATED APPLICATION

This application is a continuation-in-part of U.S. patent application Ser. No. 08/806,773 filed on Feb. 26, 1997, which is a continuation-in-part of U.S. patent application Ser. No. 08/706,576, filed Sep. 5, 1996, which is a continuation-in-part of U.S. patent application Ser. No. 08/445,849, filed May 22, 1995, now U.S. Pat. No. 5,674,895 issued Oct. 7, 1997, all assigned to ALZA Corporation of Palo Alto, Calif.

FIELD OF THE INVENTION

This invention pertains to a novel dosage form comprising oxybutynin. The invention relates also to a therapeutic composition comprising oxybutynin, to a therapeutic bilayer comprising oxybutynin, to a method for administering oxybutynin to a patient in need of oxybutynin, and to a therapeutic program for administering oxybutynin over time.

BACKGROUND OF THE INVENTION

Many people are affected by urinary incontinence. Incontinence is particularly common in the elderly; urinary incontinence is present in approximately fifty percent of nursing home patients, and urinary incontinence is a well known urologic problem in women. It will affect nearly all women in some form during their lifetime, and it is of significant social concern to all humans who experience it.

Urinary incontinence arises from the anatomy and the physiology of the urinary tract, which is composed of a bladder and a sphincter. Anatomically, the bladder consists of the bladder musculature, also known as detrusor, and the trigone. The sphincter includes the bladder neck and the proximal urethra. The detrusor muscle is innervated by the pelvic nerve through the parasympathetic nervous system, and the bladder neck and proximal urethra are innervated by the sympathetic nervous system.

The major functions of the bladder are the storage and expulsion of urine. The bladder is responsible for accommodating increasing volumes of urine at low pressures. Normally, the bladder remains closed during bladder filling and continence is maintained as long as the bladder neck and urethral pressure exceeds intravesical pressure. Voluntary voiding occurs when intravesical pressure exceeds bladder neck and urethral pressure, and involuntary voiding occurs when the intravesical pressure exceeds the bladder neck and urethral pressure.

Involuntary incontinence, also known as urge incontinence, occurs with a loss of a large volume of urine accompanied by symptoms of urgency, frequency and nocturia caused by an unstable bladder or detrusor instability. The patient may lose urine with a change in position or with auditory stimulation. The loss of small volumes of urine usually occurs because of bladder overdistension by a large amount of residual urine referred to as overflow incontinence.

The management of incontinence consists in administering a smooth muscle relaxant, such as oxybutynin, which acts directly on the smooth muscle at the site distal to the cholinergic receptor. The usual dose in the pharmacologic management is repeated doses from two-to-four times a day for oxybutynin. This is difficult to achieve as it requires rigid compliance and it is cost ineffective. Also, oxybutynin is adversely affected by light and it needs protection from air, which properties do not lend the drug to formulation into a dosage form that can administer oxybutynin at a controlled and known rate per unit time to produce the intended therapy.

In light of the above presentation it will be appreciated by those versed in the medical and pharmaceutical dispensing arts to which this invention pertains that a pressing need exists for a dosage form and for a therapeutic composition that can deliver the valuable drug oxybutynin in a controlled, extended dose to a patient in clinical need of incontinence management. The pressing need exits for an oral dosage form, for a therapeutic composition and for a method of therapy that can deliver oxybutynin at a controlled rate in a substantially constant dose per unit time for its beneficial therapeutic effect. The need exists further for a dosage form and a therapeutic composition that can deliver oxybutynin protected from light to insure that a complete dose of oxybutynin is administered to the patient and still remains substantially independent of the changing environment of the gastrointestinal tract. The need exists additionally for a sustained-release dosage form comprising the therapeutic composition that can deliver a therapeutic dose of oxybutynin for its intended effect, for avoiding an overdose, and for lessening the side effects that can accompany the drug. It will be appreciated further by those skilled in the dispensing art that if such a novel and unique dosage form, therapeutic composition and method are made available that can administer oxybutynin in a beneficial dose over time and simultaneously provide oxybutynin while lessening the incidence of both over and under dose, the dosage form, the therapeutic composition, and their accompanying methods would represent an advancement and a valuable contribution to the medical arts.

OBJECTS OF THE INVENTION

Accordingly, in view of the above presentation it is an immediate object of this invention to provide a dosage form for delivering oxybutynin in a rate-controlled dose, and which dosage form substantially overcomes the deficiencies and omissions associated with the prior art.

Another object of the present invention is to provide a sustained-release dosage form for orally administering oxybutynin in a controlled dose for the nonsurgical treatment of incontinence in a human afflicted with incontinence.

Another object of the invention is to provide a pharmacologic composition comprising oxybutynin indicated for the pharmacologic management of incontinence.

Another object of the present invention is to provide a pharmacologic composition comprising oxybutynin, its racemate, its R-enantiomer and its S-enantiomer, administrable to a human, for lessening the incidence of incontinence.

Another object of the invention is to provide a solid-oral dosage pharmaceutical form comprising a homogenous drug core for dispensing oxybutynin (or oxybutynin and its salt) to a human patient.

Another object of this invention is to provide a novel composition that makes available oxybutynin therapeutic activity to a patient in need of oxybutynin therapy.

Another object of the invention is to provide a dosage form manufactured as an osmotic dosage form that can administer oxybutynin to a biological receptor to produce the desired oxybutynin effects.

Another object of the present invention is to provide a dosage form manufactured as an osmotic dosage form that maintains oxybutynin and oxybutynin therapeutically acceptable salts in the dosage form, and thereby provides protection from light until the oxybutynin is released from the dosage form, thereby reducing and/or eliminating the unwanted influences of the gastrointestinal environment of use and still provide controlled administration of oxybutynin over time.

Another object of the present invention is to provide a dosage form that administers oxybutynin at a controlled rate over twenty-four hours for its therapeutic benefit accompanied by a lessening of possible unwanted side effects.

Another object of the present invention is to provide a dosage form that contains initially crystalline oxybutynin salt protected by a light resistant, semipermeable polymeric wall which oxybutynin can be administered in a controlled dose over time.

Another object of the present invention is to provide a dosage form adapted for the oral administration of α-cyclohexyl-αhydroxy-benzeneacetic acid 4-(diethylamino)-2-butynyl ester salt in a first composition in contacting, layered arrangement with a second, force-generating composition that operates in combination for the administration of the beneficial ester salt.

Another object of the present invention is to provide a complete pharmaceutical oxybutynin regimen comprising a composition comprising oxybutynin that can be dispensed from a drug delivery dosage form, the use of which requires intervention only for initiation and possibly for termination of the regimen.

Another object of the invention is to provide a method for treating incontinence by orally administering oxybutynin from a delivery device in a rate-controlled amount per unit time to a warm-blooded animal in need of incontinence therapy.

Another object of the invention is to provide a method of administering oxybutynin to a patient to provide a plasma concentration of oxybutynin.

Another object of the invention is to provide a therapeutic program for administering oxybutynin for the relief of bladder instability associated with urge incontinence.

Another object of the invention is to provide a method for administering oxybutynin from a controlled-release dosage form for lessening the incidence of side effects.

Another object of the invention is to provide a therapeutic program for administering oxybutynin over time to a patient in need of anticholinergic therapy.

Another object of the invention is to provide a method of administering oxybutynin in a sustained-release profile to lessen side effects.

Another object of the invention is to provide a method for administering a member selected from the group consisting of oxybutynin and its pharmaceutical salts for treating urge incontinence for zero to twenty four hours.

Other objects, features and advantages of this invention will be more apparent to those versed in the delivery arts from the following detailed specification, taken in conjunction with the accompanying claims.

BRIEF DESCRIPTION OF DRAWING FIGURES

Drawing FIG. 1 illustrates the cumulative amount of the dose released in percent for a dosage form provided by the invention.

Figure 2:
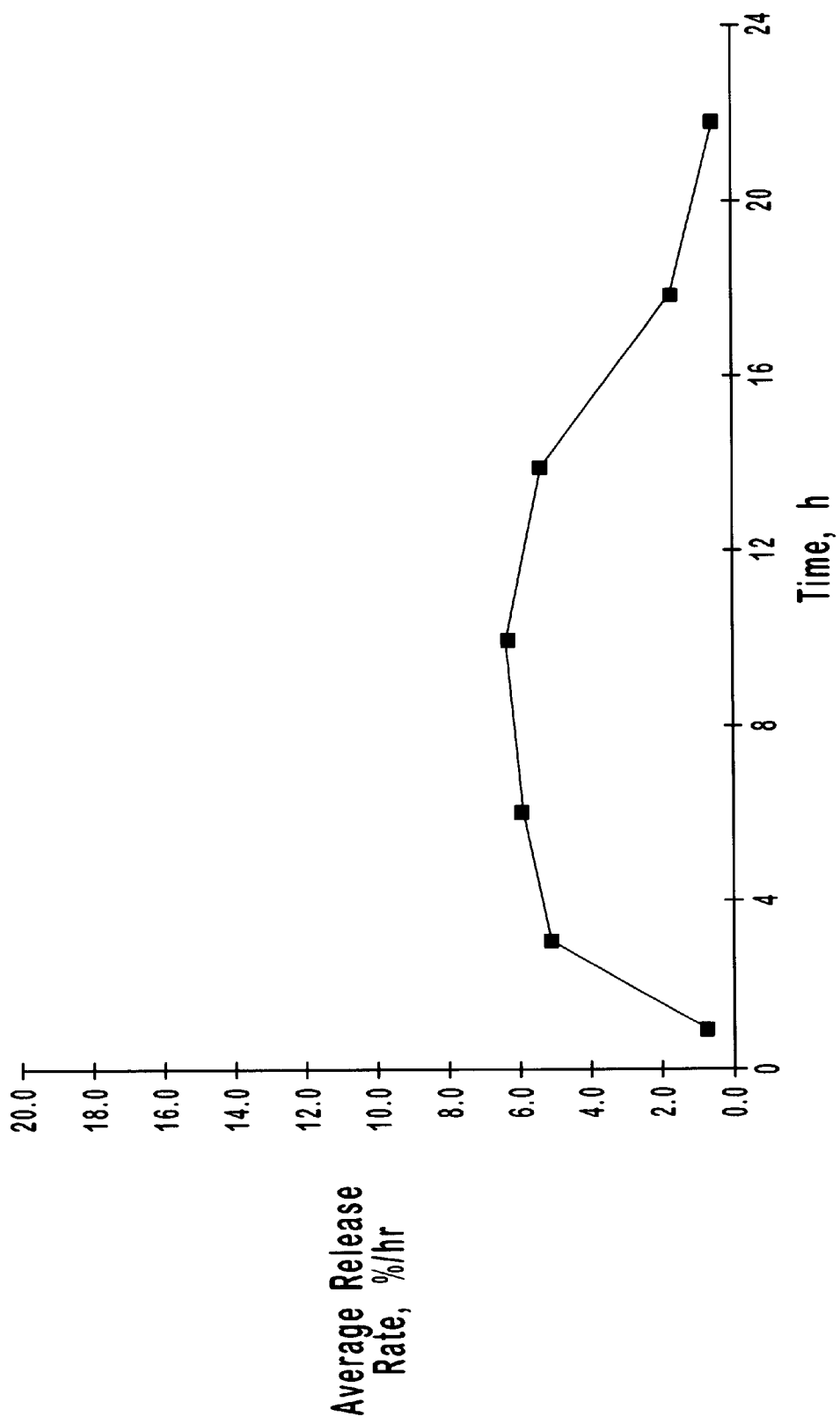

Drawing FIG. 2 illustrates the average release rate in percent per hour for a dosage form provided by the invention.

DETAILED DISCLOSURE OF SPECIFICATION

In one aspect, the present invention provides a therapeutic composition comprising 240 ng to 650 mg (nanogram to milligrams) of oxybutynin or an oxybutynin therapeutically acceptable salt. The pharmaceutically acceptable salt is selected from the group consisting of acetate, bitartrate, citrate, edetate, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate and tartrate. The drug oxybutynin can be present as the racemate, as the R-enantiomer or as the S-enantiomer. The therapeutic composition further contains 20 mg to 250 mg of a hydrogel, such as 20 mg to 250 mg of a polyalkylene oxide of 75,000 to 600,000 weight-average molecular weight. Representative polyalkylenes are a polyethylene oxide of 100,000 weight-average molecular weight, of 200,000 weight-average molecular weight or a polyethylene oxide of 300,000 weight-average molecular weight. The therapeutic composition comprises 1 mg to 50 mg of a hydroxypropylalkylcellulose of 9,000 to 150,000 average-number molecular weight selected from the group consisting of hydroxypropylmethylcellulose, hydroxypropylethylcellulose, hydroxypropylbutylcellulose, and hydroxypropylpentylcellulose; 1 mg to 40 mg of an osmotic solute selected from the osmotically effective compounds consisting of sodium chloride, potassium chloride, potassium acid phosphate, tartaric acid, citric acid, raffinose, magnesium sulfate, magnesium chloride, urea, inositol, sucrose, glucose and sorbitol; and 0.01 mg to 5 mg of a lubricant, such as calcium stearate, zinc stearate, magnesium stearate, magnesium oleate, calcium palmitate, sodium suberate, potassium laureate, salts of fatty acids, salts of alicyclic acids, salts of aromatic acids, stearic acid, oleic acid, palmitic acid, and a mixture of salt of fatty, alicyclic or aromatic acid and a fatty, alicyclic or aromatic acid.

The invention provides for the therapeutic composition comprising the drug oxybutynin to be administered as the composition neat, that is, oxybutynin alone, for increasing the urinary bladder capacity, for diminishing the frequency of uninhibited contractions of the detrusor muscles and its accompanying delay of the desire to void. The invention provides for the therapeutic oxybutynin composition to be surrounded by a wall comprising a semipermeable composition with an exit for delivering the therapeutic composition to a human patient in need of oxybutynin therapy. The invention provides, in an additional embodiment, the therapeutic composition comprising oxybutynin as a therapeutic layer in layered, contacting arrangement with a hydrogel composition manufactured as a layer that supports the therapeutic composition to yield a bilayered matrix. The hydrogel layer comprises 40 mg to 250 mg of a hydrogel, such as a member selected from the group consisting of 40 mg to 250 mg of a polyalkylene oxide of 1,500,000 to 8,000,000 weight-average molecular weight which are selected from the group consisting of polyethylene oxide and polypropylene oxide; or 40 mg to 250 mg of an alkali carboxymethylcellulose of 10,000 to 6,000,000 weight-average molecular weight such as sodium carboxymethylcellulose or potassium carboxymethylcellulose; or 0.1 mg to 250 mg of a hydroxyalkylcellulose of 7,500 to 4,500,000 weight-average molecular weight, represented by hydroxymethylcellulose, hydroxyethylcellulose, hydroxypropylcellulose, hydroxybutylcellulose, and hydroxypentylcellulose; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, diterlbutylphenol, vitamin E, lecithin and ethanolamine; and 0.1 mg to 7 mg of a lubricant selected from the group consisting of calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic or aromatic acid.

The invention provides for the therapeutic oxybutynin composition, the therapeutic bilayer comprising the drug oxybutynin layer, and the osmopolymer hydrogel layer to be administered as the composition or the bilayer per se; that is, as the composition or the bilayer together for increasing the urinary bladder capacity, for diminishing the frequency of uninhibited contractions of the detrusor muscles and its accompanying delay of the desire to void. The invention provides additionally for the therapeutic composition and the compositional bilayer to be surrounded by a wall comprising a semipermeable composition with an exit for delivering the therapeutic composition to a human patient in need of oxybutynin therapy. The invention also provides for a subcoat to surround the therapeutic composition or to surround the bilayer, which subcoat in either embodiment is surrounded by a outer semipermeable wall.

The invention provides a dosage form for the delivery of the therapeutic composition comprising oxybutynin. The dosage form comprises a wall, which wall surrounds an internal lumen or compartment. The wall comprises a semipermeable composition that is permeable to the passage of fluid and impermeable to the passage of oxybutynin. The wall is nontoxic and it comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 10 wt % of polyethylene glycol, or 1 wt % to 25 wt % of a cellulose, either selected from the group consisting of hydroxypropylcellulose or hydroxypropylalkycellulose such as hydroxypropylmethylcellulose. The total weight percent of all components comprising the wall is equal to 100 wt %. The internal compartment comprises the therapeutic oxybutynin composition in layered position with an expandable hydrogel composition. The expandable hydrogel composition in the compartment increases in dimension by imbibing the fluid through the semipermeable wall, causing the hydrogel to imbibe the fluid, expand and occupy space in the compartment, whereby the drug composition is pushed from the dosage form. The therapeutic layer and the expandable layer act together during the operation of the dosage form for the release of oxybutynin to a patient over time. The dosage form comprises a passageway in the wall that connects the exterior of the dosage form with the internal compartment. The dosage form provided by the invention delivers oxybutynin from the dosage form to the patient at a zero order rate of release over a period of 24 hours.

The expression "passageway" as used herein comprises means and methods suitable for the metered release of the therapeutic drug from the compartment of the dosage form. The exit means comprises at least one passageway, including orifice, bore, aperture, pore, porous element, hollow fiber, capillary tube, porous overlay, or porous element that provides for the osmotic controlled release of oxybutynin. The passageway includes a material that erodes or is leached from the wall in a fluid environment of use to produce at least one dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leachable polysaccharides, salts and oxides. A pore passageway, or more than one pore passageway, can be formed by leaching a leachable compound, such as sorbitol, from the wall. The passageway possesses controlled-release dimensions, such as round, triangular, square and elliptical, for the metered release of oxybutynin from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

DESCRIPTION FOR MANUFACTURING THE COMPOSITION AND DOSAGE FORM OF THE INVENTION

The wall of the dosage form can be formed by using the air suspension procedure. This procedure consists in suspending and tumbling the composition or the layers in a current of air and wall-forming composition until a wall is applied to the oxybutynin forming compartment. The air suspension procedure is well suited for independently forming the wall. The air suspension procedure is described in U.S. Pat. No. 2,799,241; J. Am. Pharm. Assoc., Vol. 48, pp. 451–459 (1959); and ibid, Vol. 49, pp. 82–84 (1960). The wall can be formed with a wall-forming composition in a Wurster® air suspension coater using an organic solvent, such as acetone-water cosolvent 90:10 (wt:wt) with 2.5 wt % to 7 wt % polymer solids. An Aeromatic® air suspension coater using, for example, a methylene dichloride methanol cosolvent comprising 87:13 (v:v) can be used for applying the wall. Other wall-forming techniques, such as pan coating system, wall forming compositions are deposited by successive spraying of the composition or the bilayered arrangement, accompanied by tumbling in a rotating pan. A larger volume of cosolvent can be used to reduce the concentration of polymer solids to produce a thinner wall. Finally, the wall of the coated compartments are laser or mechanically drilled, and then dried in a forced air or humidity oven for 1 to 3 days or longer to free the solvent. Generally, the walls formed by these techniques have a thickness of 2 to 20 mils (0.051 to 0.510 mm) with a preferred thickness of 2 to 6 mils (0.051 to 0.150 mm).

The dosage form of the invention is manufactured by standard manufacturing techniques. For example, in one manufacture the beneficial drug oxybutynin and other ingredients comprising a therapeutic composition or comprising the first layer facing the exit means are blended, or they are blended then pressed, into a solid layer. The oxybutynin and other ingredients can be blended with a solvent and formed into a solid or semisolid formed by conventional methods such as ball-milling, calendaring, stirring or roll-milling and then pressed into a selected shape. The layer posses dimensions that correspond to the internal dimensions of the area the layer is to occupy in the dosage form. The bilayer compositions possess dimensions corresponding to the internal lumen of the dosage form. Next, the oxybutynin hydrogel layer is placed in contact with the oxybutynin drug layer. The layering of the oxybutynin layer and the hydrogel layer can be fabricated by conventional press-layering techniques. Finally, the two-layer compartment forming members are surrounded and coated with an outer wall. A passageway is laser drilled or mechanically drilled through the wall to contact the oxybutynin layer, with the dosage form optically oriented automatically by the laser equipment for forming the passageway on the preselected drug surface.

In another manufacture, the dosage form is manufactured by the wet granulation technique. In the wet granulation technique the oxybutynin and the ingredients comprising the first layer are blended using an organic or inorganic solvent, such as isopropyl alcohol-methylene dichloride 80:20 (v:v) as the granulation fluid. Other granulating fluid, such as water, isopropyl alcohol, or denatured alcohol 100% can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the oxybutynin blend with continual mixing in the blender. The granulating fluid is added until a wet blend mass is produced, which wet mass is then forced through a 20 mesh screen onto oven trays. The blend is dried for 18 to 24 hours at 25° C. to 40° C. The dry granules are then screened with a 16 mesh screen. Next, a lubricant is passed through an 60 mesh screen and added to the dry screened granule blend. The granulation is put into milling jars and mixed on a jar mill for 2 to 10 minutes. The first and second layer compositions are pressed into a layered tablet, for example, in a Manesty® layer press.

Another manufacturing process that can be used for providing the oxybutynin and hydrogel composition comprises blending their powdered ingredients in a fluid bed granulator. After the powdered ingredients are dry blended in the granulator, a granulating fluid, for example, poly(vinylpyrrolidone) in a solvent, such as in water, is sprayed onto the respective powders. The coated powders are then dried in a granulator. This process coats the ingredients present therein while spraying the granulating fluid. After the granules are dried, a lubricant, such as stearic acid or magnesium stearate, is blended as above into the mixture. The granules are then pressed in the manner described above. In another embodiment, when the fluid bed granulating process is used to manufacture the hydrogel layer, the antioxidant present in the polyalkylene oxide can be removed during the processing step. If antioxidant is desired it can be added to the hydrogel formulation; this can be accomplished during the fluid bed granulation described above.

The dosage form of this invention is manufactured in another embodiment by mixing the oxybutynin with composition-forming ingredients and pressing the composition into a solid layer possessing dimensions that correspond to the internal dimensions of the compartment space adjacent to a passageway. In another embodiment, the oxybutynin and other drug composition forming ingredients and a solvent are mixed into a solid, or semi-solid, by conventional methods such as ball-milling, calendaring, stirring or roll-milling, and then pressed into a preselected, layer-forming shape.

In the manufactures as presented above, the manufacture comprising a composition or comprising a layer of a composition comprising a hydrogel osmopolymer and an optional osmagent are placed in contact with the layer comprising the drug oxybutynin, and the two layers comprising the layers are surrounded with a semipermeable wall. The layering of the first drug oxybutynin composition and the second hydrogel osmopolymer and optional osmagent composition can be accomplished by using a conventional two-layer tablet press technique. The wall can be applied by molding, spraying or dipping the pressed shapes into wall-forming materials. Another technique that can be used for applying the wall is the air suspension coating procedure. This procedure consists in suspending and tumbling the two layers in a current of air until the wall forming composition surrounds the layers. Manufacturing procedures are described in *Modern Plastics Encyclopedia,* Vol. 46, pp. 62–70 (1969); and In *Pharmaceutical* Sciences, by Remington, 14th Ed., pp. 1626–1979 (1970), published by Mack Publishing co., Easton, Pa. The dosage form can be manufactured by following the teaching in U.S. Pat. Nos. 4,327,725; 4,612,008; 4,783,337; 4,863,456; and 4,902,514.

The dissolution of a drug indicates the drug entering into solution upon its delivery from a dosage form provided by this invention is measured by the following procedure. First, a drug receiving solution, such as, gastrointestinal fluid, hydrochloride acid, or an aqueous sodium dodecyl sulfate, 1% (w/v) (weight/volume) solution is used as the dissolution media. A dosage form prepared by this invention is placed into the dissolution media and the drug released by the dosage form into the dissolution media is sampled at a constant time interval over the time period of dissolution. The filtered samples are assayed by a reversed high pressure liquid chromatography, or detection by UV. The concentration of the samples is measured against a standard curve containing, for example, at least five standard points. Procedures for dissolution testing are reported in *The United States Pharmacopoeia,* The National Formulary, pg. 1791 to 1796; (1995); *Pharmaceutical Sciences,* by Remington, 17th Ed., pg. 653–666 (1985); and USP XXII, Dissolution Paddle Analysis, pg. 1578–1579 (1990).

The release rate of drug from a dosage form manufactured by this invention can be ascertained by the following procedure. The procedure comprises placing the dosage form in a solution, usually water, and taking aliquots of the release rate solution, followed by their injection into a chromatographic system to quantify the amount of drug released during specified test intervals. The drug, for example, is resolved on a column and detected by UV absorption. Quantitation is performed by linear regression analysis of peak areas from a standard curve containing at least five standard points.

The release rate procedure comprises attaching a dosage form to a plastic rod with the orifice exposed to the drug receiving solution. Then, attaching the rod to a release arm, with the arm affixed to an up/down reciprocating shaker, which operates at an amplitude of about 3 cm and 2 seconds per cycle. Then, continuously immersing the dosage form in 50 ml test tubes containing 30 ml of $H_2O$, equilibrated in a constant temperature water bath at 37° C.±0.5° C. Next, at the end of each interval, transfer the dosage form to the next row of new test tubes containing a receiving solution, such as water. After the release pattern is complete, remove the tubes and allow to cool to room temperature, followed by filling the calibrated tubes to the 50 ml mark with a solvent, such as acetone. The samples are mixed immediately, transferred to sample vials, followed by chromatography analysis.

Exemplary solvents suitable for manufacturing the wall, the composition layers and the dosage form include inert inorganic and organic solvents that do not adversely harm the materials, the wall, the layer, the composition and the drug wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, propylene dichloride, carbon chloroform, nitroethane, nitropropane, tetrachloroethane, ethyl ether, isopropyl ether, cyclohexane, cyclo-octane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE OF EXAMPLES PROVIDED BY THE INVENTION

The following examples are merely illustrative of the present invention and they should not be considered as limiting the scope of the invention in any way, as these examples and other equivalents thereof will become apparent to those versed in the art in the light of the present disclosure and the accompanying claims.

EXAMPLE 1

A therapeutic oxybutynin composition provided by the invention was prepared as follows: first, 103 grams of oxybutynin hydrochloride was dissolved in 1200 ml (milliliters) of anhydrous ethanol. Separately, 2,280 g of polyethylene oxide of 200,000 weight-average molecular weight, 150 g of hydroxypropylmethylcellulose of 9,200 average-number molecular weight and 450 g of sodium chloride were dry blended in a conventional blender for 10 minutes to yield a homogenous blend. Next, the oxybutynin ethanol solution was added slowly to the blend, with the blender continuously blending until all the ingredients were added to the three component dry blend, with the blending continued for another 8 to 10 minutes. The blended wet composition was passed through a 16 mesh screen and dried overnight at a room temperature of 72° F. (22.2°). Then, the dry granules were passed through a 20 mesh screen, 18 g of magnesium stearate was added, and all the ingredients blended again for 5 minutes. The fresh granules are ready for formulation into a therapeutic oxybutynin composition. The therapeutic composition comprises 3.4 wt % oxybutynin hydrochloride, 76 wt % polyethylene oxide of 200,000 weight-average molecular weight, 5 wt % of hydroxypropylmethylcellulose of 9,200 average-number molecular weight, 15 wt % sodium chloride, and 0.6 wt % magnesium stearate. The therapeutic composition can be administered as the composition for its intended oxybutynin therapy.

EXAMPLE 2

An osmopolymer hydrogel composition provided by the invention was prepared as follows: first 1274 g of pharmaceutically acceptable polyethylene oxide comprising a 7,500,000 weight-average molecular weight, 600 g of sodium chloride, and 20 g ferric oxide were separately screened through a 40 mesh screen. Then, all the screened ingredients were mixed with 100 g of hydroxypropylmethylcellulose of 11,200 average-number molecular weight to produce a homogenous blend. Next, 300 ml of denatured anhydrous alcohol was added slowly to the blend with continuous mixing for 5 minutes. Then, 1.6 g of butylated hydroxytoluene was added, followed by more blending, with 5 g of magnesium stearate added with 5 minutes of blending, to yield a homogenous blend. The freshly prepared granulation is passed through a 20 mesh screen and allowed to dry for 20 hours at 22.2° C. The final composition comprised 63.67 wt % polyethylene oxide of 7,500,000 weight-average molecular weight, 30 wt % sodium chloride, 1 wt % ferric oxide, 5 mg hydroxypropylmethylcellulose of 11,200 average-number molecular weight, 0.08 wt % butylated hydroxytoluene, and 0.25 mg magnesium stearate.

EXAMPLE 3

An osmopolymer hydrogel composition provided by the invention was prepared as follows: first 1274 g of pharmaceutically acceptable sodium carboxymethylcellulose comprising a 5,250,000 weight-average molecular weight, 600 g of sodium chloride, and 20 g ferric oxide were separately screened through a 40 mesh screen. Then, all the screened ingredients were mixed with 100 g of hydroxypropylmethylcellulose of 11,200 average-number molecular weight and 100 g of hydroxypropylcellulose of 30,000 average-number molecular weight to produce a homogenous blend. Next, 300 ml of denatured anhydrous alcohol was added slowly to the blend with continuous mixing for 5 minutes. Then, 1.6 g of butylated hydroxytoluene was added, followed by more blending, with 5 g of magnesium stearate added with 5 minutes of blending, to yield a homogenous blend. The freshly prepared granulation was passed through a 20 mesh screen and allowed to dry for 20 hours at 22.2° C. The final composition comprised 58.67 wt % the sodium carboxymethylcellulose, 30 wt % sodium chloride, 1 wt % ferric oxide, 5 mg of hydroxypropylmethylcellulose, 5 mg hydroxypropylcellulose, 0.08 wt % butylated hydroxytoluene, and 0.25 mg of magnesium stearate.

EXAMPLE 4

The therapeutic oxybutynin composition and the osmopolymer hydrogel composition were made into a bilayer tablet as follows: first, 147 mg of the oxybutynin composition as prepared in Example 1 was added to a punch die set and tamped. Then, 98 mg of the hydrogel composition as prepared in Example 2 was added and the two layers compressed under a pressure head of 1.0 ton (1000 kg) into a 11/32 inch (0.873 cm) diameter, contacting intimate bilayered tablet. The example was repeated with the hydrogel composition as prepared in Example 3 to produce the tablet comprising two layers.

EXAMPLE 5

The bilayered tablet was manufactured into a dosage form as follows: first, a semipermeable wall-forming composition was prepared comprising 95 wt % cellulose acetate having a 39.8% acetyl content and 5 wt % polyethylene glycol having a number-average molecular weight of 3350 by dissolving the ingredients in a cosolvent comprising acetone and water in 90:10 wt:wt composition to make a 4% solid solution. The wall-forming composition was sprayed onto and around the bilayered cores as prepared in Examples 2 and 3 to provide a 26.4 mg semipermeable wall.

Next, the semipermeable walled, bilayered tablet was laser drilled to provide a 20 mil (0.51 mm) orifice to contact the oxybutynin layer and the exterior of the dosage form. The residual solvent was removed by drying for 48 hours at 50° C. and 50% relative humidity. Next, the dosage forms were dried further for 1 hour at 50° C. to remove excess moisture. The dosage form provided by this manufacture provides 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % magnesium stearate, and 15 wt % sodium chloride in the therapeutic oxybutynin composition. The osmopolymer hydrogel push composition comprises 63.67 wt % polyethylene oxide of 7,500,000 weight-average molecular weight, 30 wt % sodium chloride, 1 wt % ferric chloride, 5 wt % hydroxypropylmethylcellulose of 9,200 average-number molecular weight, 0.08 wt % butylated hydroxytoluene, and 0.25 wt % magnesium stearate. The semipermeable wall comprises 95 wt % cellulose acetate comprising 39.8% acetyl content, and 5 wt % polyethylene glycol of 3350 number-average molecular weight. The dosage form comprises an exit passage of 20 mils (0.50 mm) and it has a mean release rate of 0.260 mg/hr for 23.8 hours. The semipermeable wall provides substantial protection from photo (light) degradation of the oxybutynin in the dosage form.

EXAMPLE 6

A dosage form is prepared according to the above examples, comprising a drug layer consisting of 6.67 wt % oxybutynin hydrochloride, 87.83 wt % polyethylene oxide of 200,000 weight-average molecular weight, 5.00 wt % hydroxypropylmethylcellulose of 9,200 average-number molecular weight, and 0.50 wt % magnesium stearate; in layered contact with a push hydrogel layer comprising 58.75 wt % sodium carboxymethylcellulose of 6,000,000 weight-average molecular weight, 30 wt % sodium chloride, 5.00 wt % hydroxypropylmethylcellulose of 9,200 average-number molecular weight, 1.00 wt % ferric oxide, 5.00 wt % hydroxypropylcellulose of 75,000 average-number molecular weight and 0.25 wt % magnesium stearate; which bilayered core is surrounded by a semipermeable wall comprising cellulose acetate and polyethylene glycol; and an exit port through the wall for delivering the oxybutynin at a controlled rate over thirty hours.

EXAMPLE 7

The dosage form according to Example 6 wherein the polyethylene oxide has a 300,000 weight-average molecular weight; the hydroxypropylcellulose is a member selected from the group consisting of 25,000, 30,000 or 40,000 average-number molecular weight; and the dosage form comprises 5 mg to 250 mg of oxybutynin pharmaceutically acceptable salt.

EXAMPLE 8

A dosage form was prepared according to the above examples wherein the dosage form of this example comprises a drug oxybutynin layer comprising 5 mg oxybutynin, 111.60 mg polyethylene oxide of 200,000 weight-average molecular weight, 7.35 mg hydroxypropylmethylcellulose of 9,200 average-number molecular weight, 0.88 mg magnesium stearate, 22.05 mg of sodium chloride, and 0.12 mg of butylated hydroxytoluene; a hydrogel push layer comprising 62.40 mg of polyethylene oxide of 7,000,000 weight-average molecular weight, 29.40 mg of sodium chloride, 4.90 mg hydroxypropylmethylcellulose of 9,200 average-number molecular weight, 0.08 mg of butylated hydroxytoluene, 0.98 mg of red ferric oxide, and 0.24 mg of magnesium stearate; a wall comprising cellulose acetate consisting of a 39.8% acetyl content and polyethylene glycol of 3350 number-average molecular weight in the percentage ratio of 95 wt % cellulose acetate to 5 wt % polyethylene glycol, and an exit passageway in the wall.

EXAMPLE 9

A dosage form was prepared according to the examples provided by this invention wherein the dosage form comprises: a drug oxybutynin layer comprising 5.3 wt % oxybutynin, 82.37 wt % polyethylene oxide of 200,000 weight-average molecular weight, 2 wt % hydroxypropylmethylcellulose of 9,200 average-number molecular weight, 0.25 wt % magnesium stearate, 10 wt % sodium chloride, and 0.08 wt % butylated hydroxytoluene; a push hydrogel layer comprising 63.37 wt % polyethylene oxide of 2,000,000 weight-average molecular weight, 30 wt % sodium chloride, 5 wt % hydroxypropyl-methylcellulose of 9,200 average-number molecular weight, 0.08 wt % butylated hydroxytoluene, 1 wt % black ferric oxide and 0.25 wt % magnesium stearate; a wall comprising 99 wt % cellulose acetate comprising a 39.8% acetyl content and 1 wt % polyethylene glycol of 3350 number-average molecular weight; and an exit passageway through the wall for delivering the oxybutynin to a patient.

EXAMPLE 10

An oxybutynin composition was prepared according to the above examples, wherein the composition comprises 10.6 wt % oxybutynin hydrochloride, 79.57 wt % polyethylene oxide of 200,000 weight-average molecular weight, 2 wt % hydroxypropylmethylcellulose of 9,200 average-number molecular weight, 0.25 wt % of magnesium stearate, 7.5 wt % of sodium chloride, and 0.08 wt % butylated hydroxytoluene.

EXAMPLE 11

An oxybutynin composition was prepared according to the above examples wherein the composition comprises 16 wt % oxybutynin hydrochloride, 76.67 wt % polyethylene oxide of 200,000 weight-average molecular weight, 2 wt % hydroxypropylmethylcellulose of 9,200 average-number molecular weight, 0.25% magnesium stearate, 5 wt % sodium chloride and 0.08 wt % butylated hydroxytoluene.

EXAMPLE 12

A hydrogel composition was prepared according to the above examples wherein the composition comprises 58.75 wt % hydroxyethylcellulose of 1,300,000 molecular weight, 30 wt % sodium chloride, 10 wt % polyvinylpyrrolidone of 42,000 viscosity-average molecular weight, 1 wt % red ferric oxide, and 0.25 wt % magnesium stearate.

EXAMPLE 13

A dosage form was prepared according to the present invention wherein the dosage form comprises: a drug layer comprising 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % magnesium stearate, 15 wt % sodium chloride; a push hydrogel layer comprising 58.75 wt % hydroxyethylcellulose of 1,300,000 average-number molecular weight, 30 wt % sodium chloride, 10 wt % polyvinylpyrrolidone of 42,000 viscosity-average molecular weight, 1 wt % red ferric oxide, and 0.25 wt % magnesium stearate; a wall comprising 95 wt % cellulose acetate comprising a 39.8% acetyl content, and 5 wt % polyethylene glycol of 3350 number-average molecular weight, an exit orifice of 20 mil (0.50 mm); and a release rate of 0.292 mg per 1 hour for 16.9 hours.

EXAMPLE 14

A dosage form was manufactured according to the present examples wherein the dosage form comprises: a drug oxybutynin layer comprising 3.4 wt % oxybutynin hydrochloride, 76 wt % polyethylene oxide of 200,000 weight-average molecular weight, 5 wt % hydropropylmethylcellulose of 9,200 average-number molecular weight, 0.6 wt % of magnesium stearate, and 15 wt % sodium chloride; a push hydrogel layer for pushing the drug oxybutynin layer form the dosage form comprising 63.67 wt % polyethylene oxide of 7,000,000 weight-average molecular weight, 30 wt % sodium chloride, 1 wt % red ferric oxide, 5 wt % hydroxypropylmethylcellulose of 9,200 average-number molecular weight, 0.08 wt % butylated hydroxytoluene, and 0.25 wt % magnesium stearate; a subcoat that surrounds the drug oxybutynin layer and push hydrogel layer wherein the subcoat comprises 95 wt % hydroxyethyl-cellulose, a nonionic water soluble polymer of 90,000 average-number molecular weight; a wall or overcoat comprising 95 wt % cellulose acetate possessing an acetyl content of 39.8% and 5 wt % polyethylene glycol of 3,350 number-average molecular weight; a 20 mil (0.50 mm) exit passageway; and an oxybutynin release rate of 0.295 mg per 1 hour over 19.9 hours.

EXAMPLE 15

A dosage form designed and shaped as a pharmaceutically acceptable tablet for the oral administration of a member selected from the group consisting of oxybutynin and its pharmaceutically acceptable salts was made by following the above examples. The dosage form provided by the example comprises a drug composition weighing 92 mg comprising 5.45 wt % of oxybutynin hydrochloride, 9.98 wt % of sodium chloride, 82.16 wt % of polyethylene oxide of 100,000 molecular weight, 2.00 wt % of hydroxypropylmethylcellulose of 11,300 molecular weight, 0.25 wt % of magnesium stearate, 0.08 wt % of butylated hydroxytoluene, and 0.05 wt % of green ferric oxide. The composition was surrounded by a wall comprising a semipermeable cellulose acetate polymer comprising a 39.8% acetyl content and polyethylene glycol comprising a 3,350 molecular weight. The dosage form comprised can exit for delivering oxybutynin to the gastrointestinal tract of a patient.

EXAMPLE 16

A dosage form adapted as an orally administrable tablet was made according to the above examples. The dosage form of this example comprises a drug composition weighing 92 mg and comprising 5.45 wt % oxybutynin hydrochloride, 9.98 wt % sodium chloride, 82.19 wt % polyethylene oxide possessing a 200,000 molecular weight, 2.00 wt % hydroxypropylmethylcellulose of 11,300 molecular weight, 0.25 wt % magnesium stearate, 0.08 wt % butylated hydroxytoluene, and 0.05 wt % green ferric oxide; a push composition initially in contact with the drug composition, weighing 62 mg and comprising 63.67 wt % polyethylene oxide possessing a 2,000,000 molecular weight, 30.00 wt % sodium chloride, 5.00 wt % hydroxypropylmethylcellulose of 11,200 molecular weight, 1.00 wt % of a 95.5 mixture of black iron oxide/lactose, 0.25 wt % magnesium stearate, and 0.08 wt % butylated hydroxytoluene; a wall weighing 19 mg that surrounds the compositions and comprises 99 wt % of cellulose acetate of 39.8% acetyl content, and 1.00 wt % polyethylene glycol of 3,350 molecular weight; a yellow color overcoat weighing 100 mg; and an exit in the wall for delivering the drug to a patient. The dosage form exhibited a cumulative release of oxybutynin hydrochloride of greater than zero mg to 1 mg in 0 to 4 hours, 1 mg to 2.5 mg in 0 to 8 hours, 2.75 mg to 4.25 mg in 0 to 14 hours, and 3.75 mg to 5 mg in 0 to 24 hours.

EXAMPLE 17

A dosage form for the oral administration of oxybutynin was made by following the above examples. The dosage form comprises a 92 mg drug composition comprising 10.90 wt % oxybutynin hydrochloride, 7.48 wt % sodium chloride, 79.25 wt % polyethylene oxide possessing a 200,000 molecular weight, 1.99 wt % hydroxypropylmethylcellulose possessing a 11,300 molecular weight, 0.25 wt % magnesium stearate, 0.08 wt % butylated hydroxytoluene, and 0.05 wt % red ferric oxide; a push composition weighing 62 mg and comprising 63.67 wt % polyethylene oxide possessing a 2,000,000 molecular weight, 30 wt % sodium chloride, 5 wt % hydroxypropylmethylcellulose possessing a 11,300 molecular weight, 1.00 wt % black iron oxide/lactose (95:5), 0.25 wt % magnesium stearate, and 0.08 wt % butylated hydroxytoluene; a wall that envelopes the compositions weighing 19 mg comprising 99 wt % cellulose acetate comprising a 39.8 acetyl content, and 1 wt % polyethylene glycol 3350; a exit in the wall; and a 10 mg push overcoat. The dosage form delivers in 0 to 4 hours up to 20% (up to 2 mg) of oxybutynin hydrochloride, in 0 to 8 hours 20 to 50% (2.0 to 5.0 mg) of oxybutynin salt; in 0 to 14 hours 50 to 85% (5.5 mg to 8.5 mg) of oxybutynin; and 0 to 24 hours greater than 75% (greater than 7.5 mg) of the drug.

EXAMPLE 18

A dosage form for the oral delivery of a member selected from the group consisting of oxybutynin and its pharmaceutically acceptable salts was made according to the above examples. The dosage form comprised a drug layer weighing 92 mg comprising 16.30 wt % oxybutynin chloride, 4.98 wt % sodium chloride, 76.35 wt % polyethylene oxide of 200,000 molecular weight, 1.99 wt % hydroxypropylmethylcellulose, 0.25 wt % magnesium stearate, 0.08 wt % butylated hydroxytoluene, 0.02 wt % black iron oxide/lactose (95:5); a push composition weighing 62 mg comprising 63.67 wt % polyethylene oxide possessing a 2,000,000 molecular weight, 30.00 wt % sodium chloride, 5.00 hydroxypropylmethylcellulose of 11,300 molecular weight, 1.00 wt % black iron oxide/lactose (95:5), 0.25 wt % magnesium stearate, and 0.08 wt % butylated hydroxytoluene; a wall weighing 19 mg comprising a composition permeable to fluid flux, impermeable to drug flux comprising 99.00 wt % cellulose acetate having a 39.8 acetyl content, and 1.00 wt % polyethylene glycol 3350; a passageway in the wall; and a overcoat weighing 10 mg colored grey. The dosage form exhibited a cumulative release rate of up to 3 mg in 0 to 4 hours; 3 mg to 7.5 mg in 0 to 8 hours; 8 mg to 13 mg in 0 to 14 hours; and 12 mg to 15 mg in 0 to 24 hours.

EXAMPLE 19

A dosage form was prepared according to the previous examples comprising an oxybutynin salt, that delivers up to 1.60 mg in 0 to 4 hours, up to 5 mg in 0 to 8 hours, up to 8.5 mg in 0 to 12 hours, up to 11 mg in 0 to 16 hours, and up to 15 mg in 0 to 24 hours.

EXAMPLE 20

A solid, orally administrable dosage form comprising 1 mg to 100 mg of a drug selected from the group consisting of oxybutynin and its pharmaceutically acceptable salt is prepared by following the previous examples.

EXAMPLE 21

Dosage forms for administering oxybutynin were prepared according to the above examples, and the oxybutynin release rate profile are illustrated in FIGS. 1 and 2. FIG. 1 depicts the cumulative amount of the dose released normalized to the percent of the dose released from dosage forms comprising 5 mg, 10 mg, and 15 mg of oxybutynin. FIG. 2 depicts the average release rate expressed as percent of the total dose per hour for dosage forms comprising 5 mg, 10 mg, and 15 mg of oxybutynin.

METHOD OF PRACTICING THE INVENTION

The invention pertains additionally to the use of the therapeutic composition and the dosage form by providing a method for delivering oxybutynin orally to a warm-blooded animal, including a human patient, in need of oxybutynin therapy. The method comprises administering orally the composition to a patient for oxybutynin therapy. The method comprises: (A) admitting orally into the patient a dosage form comprising (B) a semipermeable wall that surrounds (C) a therapeutic composition comprising (A) oxybutynin. The dosage form imbibes fluid through the wall into the dosage form in response to the concentration gradient across the semipermeable wall. The therapeutic composition in the dosage form develops osmotic energy that causes the therapeutic composition to be administered through the exit (D) from the dosage form over a prolonged period of time up to 24 hours to provide controlled and sustained oxybutynin therapy. The method of the invention comprises also: (A) admitting into the warm-blooded animal a dosage form comprising: (1) a wall surrounding a compartment, the wall comprising a semipermeable polymeric composition permeable to the passage of fluid and substantially impermeable to the passage of oxybutynin; (2) an oxybutynin drug layer in the compartment comprising oxybutynin; (3) a hydrogel push layer in the compartment comprising an osmotic formulation for imbibing and absorbing fluid for expanding in size for pushing the oxybutynin composition from the delivery device; and (4) at least one passageway in the wall for releasing the oxybutynin; (B) imbibing fluid through the semipermeable wall at a fluid-imbibing rate determined by the permeability of the semipermeable wall and the osmotic pressure across the semipermeable wall causing the push layer to expand; and (C) delivering the therapeutically active oxybutynin from the delivery device through the exit passageway to a warm-blooded animal over a prolonged period of time up to 24 hours. The oxybutynin is administered by the method of the invention in the therapeutic range that avoids a toxic dose and avoids an ineffective dose for antispasmodic therapy. The oxybutynin is administered to patients with uninhibited neurogenic and reflex neurogenic bladder for increase vessel capacity which diminishes the frequency of uninhibited contractions of the detrusor muscle and delays the desire to void. The dosage form is indicated for the relief of symptoms associated with voiding such as urgency, urge incontinence, frequency, nocturia and incontinence in patients in neurogenic bladder.

The drug oxybutynin, identified as OXY, was administered in a clinical study to a number of patients. Oxybutynin is used for treating urinary-incontinence. Patients administered oxybutynin often quit or discontinue treatment in the prior art due to its anti-cholinergic side effects, which appear to be peak-concentration related. The present invention provides a controlled-release (CR) oral dosage form comprising oxybutynin designed to provide a continuous plasma drug concentration and avoid peak concentrations. That is, the controlled-extended release dosage form of this invention maintains a therapeutic plasma concentration free of an overdose and free of an ineffective underdose of oxybutynin. In a multiple dose, crossover study, 13 healthy female volunteers of 41 to 68 years of age received either 5 mg of oxybutynin immediate release (IR) every 8 hours, or three 5 mg controlled release (CR) once a day, for four days. The patients blood was sampled on days 1 and 4 to quantify oxybutynin and its desethylmetabolite (DESOXY) by liquid chromatography mass spectroscopy (LC/MS). The oxybutynin was absorbed rapidly following immediate-release (IR) dosing with mean $C_{max}$ of 12 ng/ml. $C_{max}$ is the maximum concentration after dosing in the plasma. The drug release kinetics for the controlled-release (CR) plasma concentration rose slowly, reaching a mean $C_{max}$ value of 4.2–6.7 ng/ml. The metabolite DESOXY was formed rapidly following immediate release, and its formation paralleled the slow absorption of oxybutynin following controlled release. The DESOXY had a shorter $t_{1/2}$ life compared to OXY, indicating presystemic metabolite formation assuming it to be true metabolite $t_{1/2}$. Single and multiple dose AUC values were similar for both the controlled release and the immediate release suggesting time invariant pharmacokinetics. AUC denotes the area under the plasma concentration profile. The day 4 OXY and DESOXY AUC and their ratios are presented in the Table, where BA denotes the percent bioavailable, that is, BA denotes the relative amount of oxybutynin absorbed from the controlled release (CR) dosage form compared to the immediate release (IR) dosage form, and $C_{max}$ denotes the maximum concentration.

|    | OXY (AUC) (ng.h/mL) | DESOXY (AUC) (ng.h/mL) | OXY/DESOXY Ratio | OXY (BA %) | DESOXY (BA %) |
| --- | --- | --- | --- | --- | --- |
| IR | 81 | 483 | 0.18 | | |
| CR | 109 | 304 | 0.41 | 153 | 69 |

The higher ratio of OXY-BA following CR compared to IR suggests lower metabolic formation on first pass. This indicates CR could reach the colon within 3–5 hours post dosing. Presystemic cytochrome P450-mediated oxidation may occur in the upper part of the gastrointestinal tract; then, drug release from CR in the colon escapes presystemic metabolism, which could explain the higher OXY/DESOXY ratio and increased OXY BA following CR.

The dosage form and the oxybutynin composition of this invention, as seen from the above disclosure, can be used in a method for administering a drug by the oral route, and, in another method, the dosage form and composition can be sized and shaped for administering a drug by the sublingual and buccal routes. The sublingual and buccal routes can be used for quicker therapy, and they can be used when a smaller dose of drug is needed for immediate therapy. The latter routes can be used as a by-pass of the first pass of heptic metabolism of the drug.

In summary, it will be appreciated that the present invention contributes to the art an unobvious dosage form that possesses practical utility, can administer a drug at a dose-metered release rate per unit time. While the invention has been described and pointed out in detail with reference to operative embodiments thereof, it will be understood by those skilled in the art that various changes, modifications, substitutions an omissions can be made without departing from the spirit of the invention. It is intended, therefore, that the invention embrace those equivalents within the scope of the claims which follow.

We claim:

1. A sustained-release oxybutynin formulation for oral administration to a patient comprising a therapeutic dose of an oxybutynin selected from the group consisting of oxybutynin and its pharmaceutically acceptable salt that delivers from 0 to 20% of the oxybutynin in 0 to 4 hours, from 20 to 50% of the oxybutynin in 0 to 8 hours, from 50 to 85% of the oxybutynin in 0 to 14 hours, and greater than 75% of the oxybutynin in 0 to 24 hours for treating incontinence in the patient.

2. A sustained-release oxybutynin formulation for oral administration to a patient in need of treatment for urge incontinence comprising a therapeutic dose of an oxybutynin selected from the group consisting of oxybutynin and its pharmaceutically acceptable salt that delivers from 0 to 1 mg in 0 to 4 hours, from 1 mg to 2.5 mg in 0 to 8 hours, from 2.75 to 4.25 mg in 0 to 14 hours, and 3.75 mg to 5 mg in 0 to 24 hours for treating urge incontinence in the patient.

3. A sustained-release oxybutynin solid dosage form for oral administration to a patient for treating incontinence comprising an oxybutynin selected from the group consisting of oxybutynin and its pharmaceutically acceptable salt that administers up to 2 mg of the member in 0 to 4 hours, from 2 mg to 5 mg of the member in 0 to 8 hours, from 5 mg to 8.5 mg of the member in 0 to 14 hours, and greater than 7.5 mg in 0 to 24 hours for treating incontinence in the patient.

4. A sustained-release oxybutynin dosage form for oral administration to a patient for treating incontinence comprising an oxybutynin selected from the group consisting of oxybutynin and its pharmaceutically acceptable salt that administers up to 3 mg in 0 to 4 hours, 3 mg to 7.5 mg in 0 to 8 hours, 8 mg to 13 mg in 0 to 14 hours, and 12 mg to 15 mg in 0 to 24 hours for treating incontinence in the patient.

5. A dosage form for the oral administration of oxybutynin to a patient for treating incontinence, wherein the dosage form comprises a therapeutic dose of oxybutynin that is administered in a sustained-release cumulative dose of 0.2% to 80% over 2 to 16 hours.

6. The dosage form for the oral administration of oxybutynin according to claim 5, wherein the dosage form comprises a dose of 5 mg to 20 mg of oxybutynin.

7. The dosage form for the oral administration of oxybutynin according to claim 5, wherein the dosage form is a pharmaceutically acceptable tablet.

8. A dosage form for the oral administration of oxybutynin to a patient for treating incontinence, wherein the dosage form comprises a therapeutic dose of oxybutynin that is administered in a sustained release rate of 0.5% to 7% per hour over 30 minutes to 22 hours.

9. The dosage form for the oral administration of oxybutynin according to claim 8, wherein the dosage form comprises a dose of 5 mg to 20 mg of oxybutynin.

10. The dosage form for the oral administration of oxybutynin according to claim 8, wherein the dosage form is a pharmaceutically acceptable solid tablet.

11. A method for treating incontinence in a patient, wherein the method comprises administering orally to the patient a therapeutic dose of an oxybutynin selected from the group consisting of oxybutynin and its pharmaceutically acceptable salt that is delivered from 0 to 20% of the dose in 0 to 4 hours, from 20 to 50% of the dose in 0 to 8 hours, from 50 to 85% of the dose in 0 to 14 hours, and greater than 75% of the dose in 0 to 24 hours for treating incontinence in the patient.

12. The method for treating incontinence in a patient according to claim 11, wherein the therapeutic dose is 1 mg to 100 mg.

13. A method for treating incontinence in a patient, wherein the method comprises administering orally to the patient a therapeutic dose of an oxybutynin selected from the group consisting of oxybutynin and its pharmaceutically acceptable salt which oxybutynin is administered in from 0 to 1 mg in 0 to 4 hours, from 1 mg to 2.5 mg in 0 to 8 hours, from 2.75 to 4.25 mg in 0 to 14 hours, and 3.75 mg to 5 mg in 0 to 24 hours for treating incontinence in the patient.

14. A method for treating incontinence in a patient, wherein the method comprises administering orally to the patient a therapeutic dose of an oxybutynin and its pharmaceutically acceptable salt, which oxybutynin is administered in up to 2 mg in 0 to 4 hours, 2 mg to 5 mg in 0 to 8 hours, 5 mg to 8 mg in 8.5 mg in 0 to 14 hours, and greater than 7.5 mg in 0 to 24 hours for treating incontinence in the patient.

15. A method for treating incontinence in a patient, wherein the method comprises administering orally to the patient a therapeutic dose of an oxybutynin selected from the group consisting of oxybutynin and its pharmaceutically acceptable salt, which oxybutynin is administered in up to 3 mg in 0 to 4 hours, 3 mg to 7.5 mg in 0 to 8 hours, 8 mg to 13 mg in 0 to 14 hours, and 12 mg to 15 mg in 0 to 24 hours for treating incontinence in the patient.

16. A method for treating incontinence in a patient, wherein the method comprises administering orally to the patient a dosage form comprising a therapeutic dose of oxybutynin that is administered in a sustained-release cumulative dose of 0.2% to 80% over 2 to 16 hours for treating incontinence.

17. The method for treating incontinence in a patient according to claim 16, wherein the therapeutic dose comprises 5 to 15 mg of oxybutynin.

18. The method for treating incontinence in a patient according to claim 16, wherein the dosage form is a pharmaceutically acceptable tablet.

19. A method for treating incontinence in a patient, wherein the method comprises administering orally to the patient a dosage form comprising a therapeutic dose of oxybutynin that is administered in a sustained release rate of 0.5% to 7% per hour over 30 minutes to 22 hours for treating incontinence.

20. The method for treating incontinence in a patient according to claim 19, wherein the therapeutic dose comprises 5 to 15 mg of oxybutynin.

21. The method for treating incontinence in a patient according to claim 19, wherein the dosage form is a pharmaceutically acceptable tablet.

* * * * *